(12) United States Patent
Nishigishi et al.

(10) Patent No.: US 8,858,530 B2
(45) Date of Patent: Oct. 14, 2014

(54) CATHETER

(71) Applicant: Asahi Intecc Co. Ltd., Nagoya (JP)

(72) Inventors: Makoto Nishigishi, Owariasahi (JP);
Fumiyoshi Ashima, Nagoya (JP);
Shuichi Kuwada, Seto (JP)

(73) Assignee: Asahi Intecc Co., Ltd., Nagoya-shi (JP)

( * ) Notice: Subject to any disclaimer, the term of this patent is extended or adjusted under 35 U.S.C. 154(b) by 0 days.

(21) Appl. No.: 13/903,437

(22) Filed: May 28, 2013

(65) Prior Publication Data

US 2014/0031796 A1 Jan. 30, 2014

(30) Foreign Application Priority Data

Jul. 30, 2012 (JP) .................................. 2012-167990

(51) Int. Cl.
*A61M 1/00* (2006.01)
*B29C 70/54* (2006.01)
*B29C 70/22* (2006.01)
*A61M 25/00* (2006.01)
*B29L 31/00* (2006.01)
*A61M 25/01* (2006.01)

(52) U.S. Cl.
CPC ... *A61M 25/0052* (2013.01); *A61M 2025/0081* (2013.01); *B29L 2031/7542* (2013.01); *A61M 25/0012* (2013.01); *A61M 25/005* (2013.01); *B29C 70/543* (2013.01); *A61M 25/0053* (2013.01); *A61M 25/0108* (2013.01); *B29C 70/22* (2013.01); *A61M 25/0054* (2013.01)
USPC ........... 604/527; 604/526; 604/524; 138/123; 138/127

(58) Field of Classification Search
CPC .......... A61M 25/001; A61M 25/0012; A61M 25/005; A61M 25/0053
USPC .......... 604/523–527; 138/118, 123–127, 135; 174/117 M, 357
See application file for complete search history.

(56) References Cited

U.S. PATENT DOCUMENTS

| 5,509,910 A | 4/1996 | Lunn |
| 6,511,462 B1 | 1/2003 | Itou et al. |

(Continued)

FOREIGN PATENT DOCUMENTS

| CA | 2 348 523 C | 6/2000 |
| CA | 2 603 109 C | 6/2000 |

(Continued)

OTHER PUBLICATIONS

Dec. 18, 2013 Search Report issued in European Patent Application No. 13171185.5.

*Primary Examiner* — Bhisma Mehta
*Assistant Examiner* — William Frehe
(74) *Attorney, Agent, or Firm* — Oliff PLC

(57) ABSTRACT

A catheter includes an inner layer, a braid, an outer layer, and a distal tip. A recessed region having a first side and a second side is formed in a distal end portion of the braid, a length of the first side being longer than the sum of a wire width of a first wire and a distance between two adjacent first wires, a length of the second side being longer than the sum of a wire width of a second wire and a distance between two adjacent second wires. The distal tip is bonded to the inner layer in the recessed region. By providing the recessed region, the number of peaks formed in the distal end portion of the braid is made smaller than that in the existing case.

14 Claims, 7 Drawing Sheets

(56) References Cited

U.S. PATENT DOCUMENTS

| | | |
|---|---|---|
| 6,648,874 B2 | 11/2003 | Parisi et al. |
| 6,689,120 B1 * | 2/2004 | Gerdts .................. 604/526 |
| 7,597,830 B2 | 10/2009 | Zhou |
| 8,475,431 B2 | 7/2013 | Howat |
| 2001/0027310 A1 | 10/2001 | Parisi et al. |
| 2001/0051790 A1 | 12/2001 | Parker |
| 2005/0010194 A1 | 1/2005 | Zhou |
| 2008/0125752 A1 * | 5/2008 | Gunderson et al. ......... 604/527 |
| 2010/0016837 A1 | 1/2010 | Howat |
| 2011/0224628 A1 | 9/2011 | Bodenlenz et al. |
| 2012/0109078 A1 | 5/2012 | Schaeffer |
| 2013/0255062 A1 | 10/2013 | Howat |

FOREIGN PATENT DOCUMENTS

| | | |
|---|---|---|
| CA | 2 401 128 C | 9/2001 |
| CA | 2 660 412 A1 | 2/2008 |
| CA | 2 737 634 A1 | 3/2010 |
| EP | 1 068 876 B1 | 1/2001 |
| EP | 1 259 270 B1 | 3/2006 |
| EP | 2 453 967 B1 | 5/2013 |
| EP | 2 326 379 B1 | 7/2013 |
| JP | A-2001-87389 | 4/2001 |
| JP | A-2011-72562 | 4/2011 |
| WO | WO 00/35527 | 6/2000 |
| WO | WO 2008/019236 A1 | 2/2008 |
| WO | WO 2010/031515 A1 | 3/2010 |
| WO | WO 2011/008738 A1 | 1/2011 |

* cited by examiner

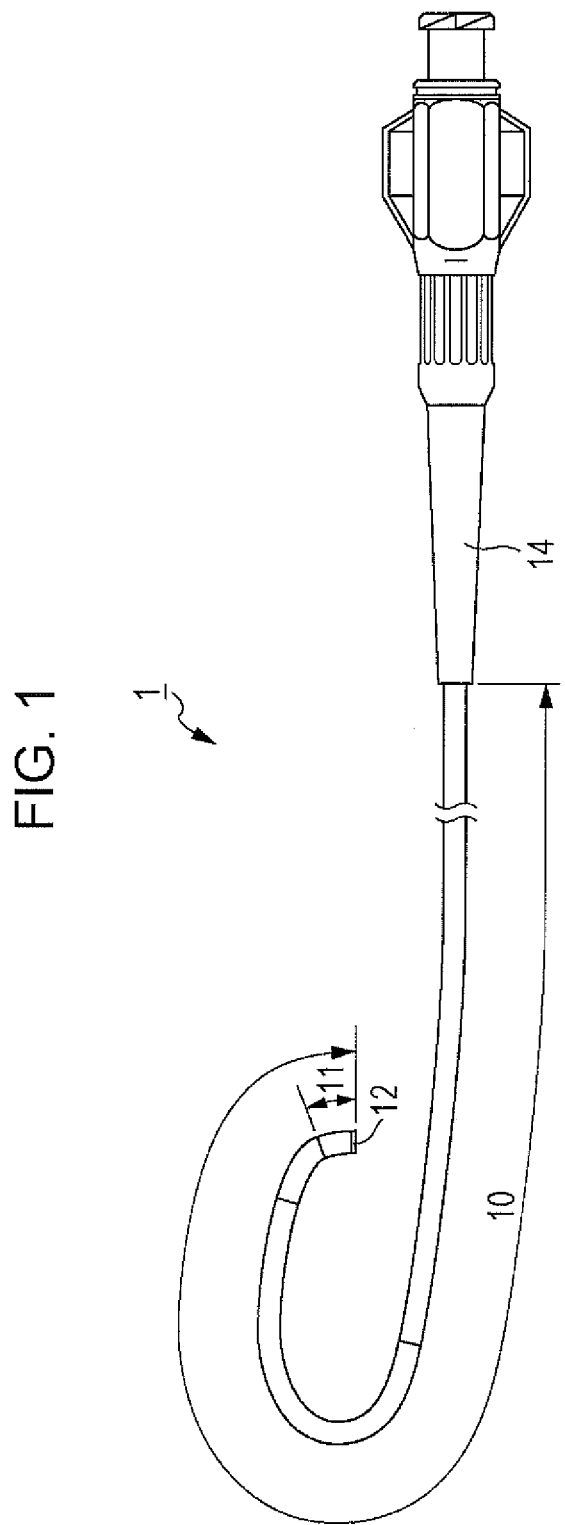

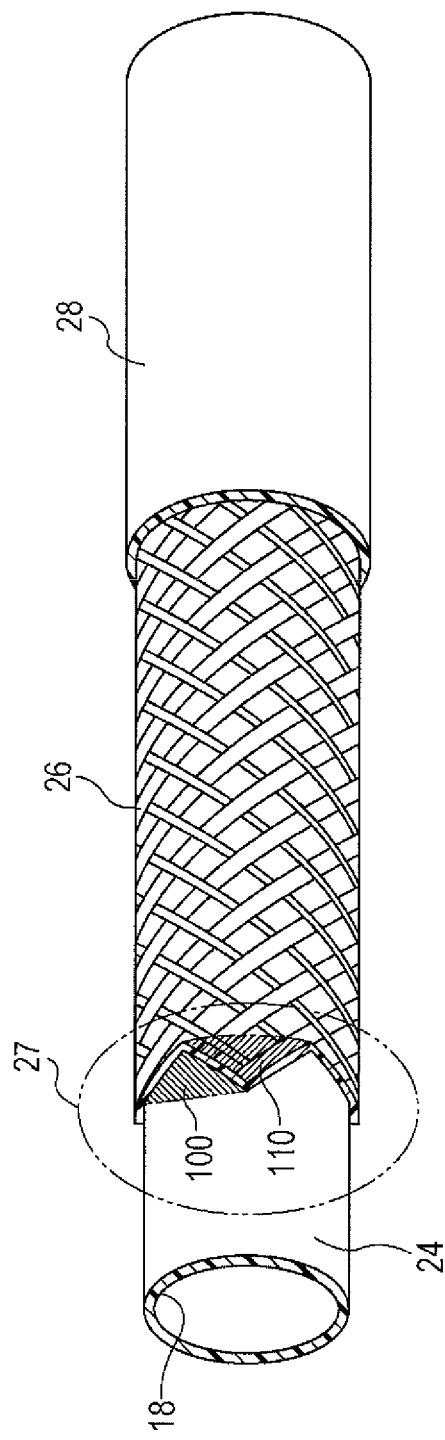

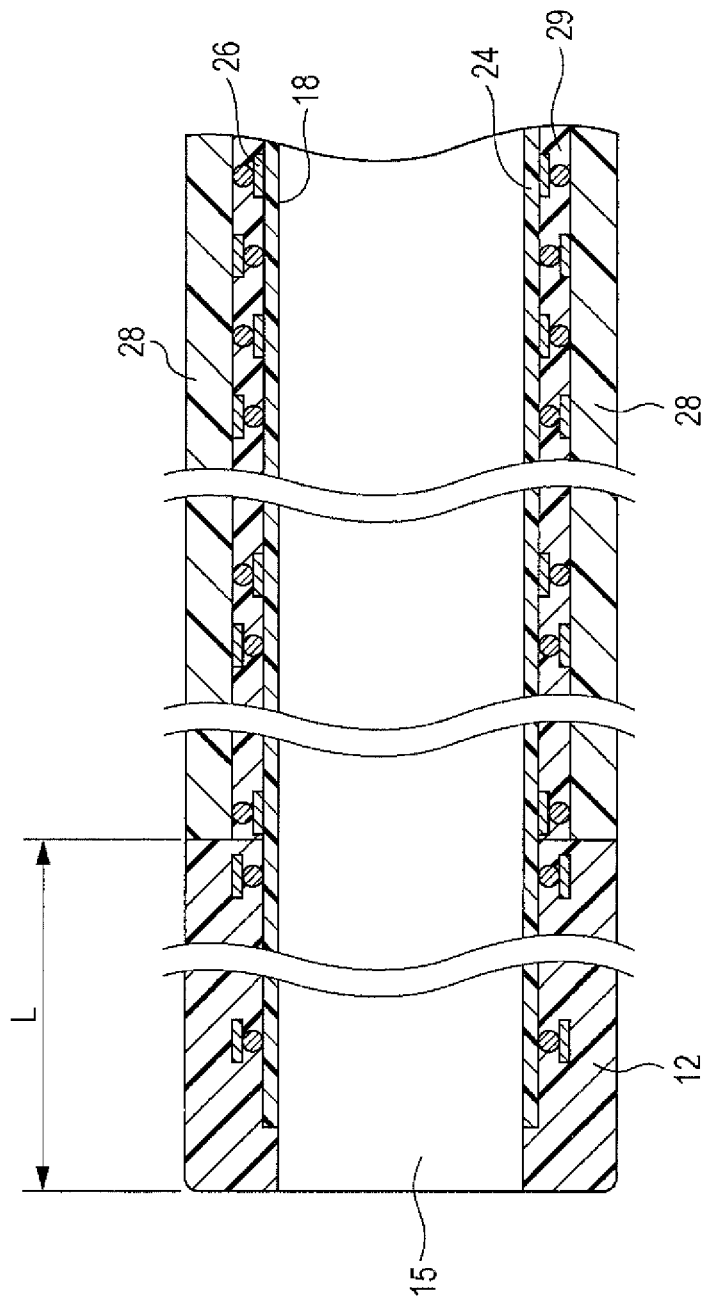

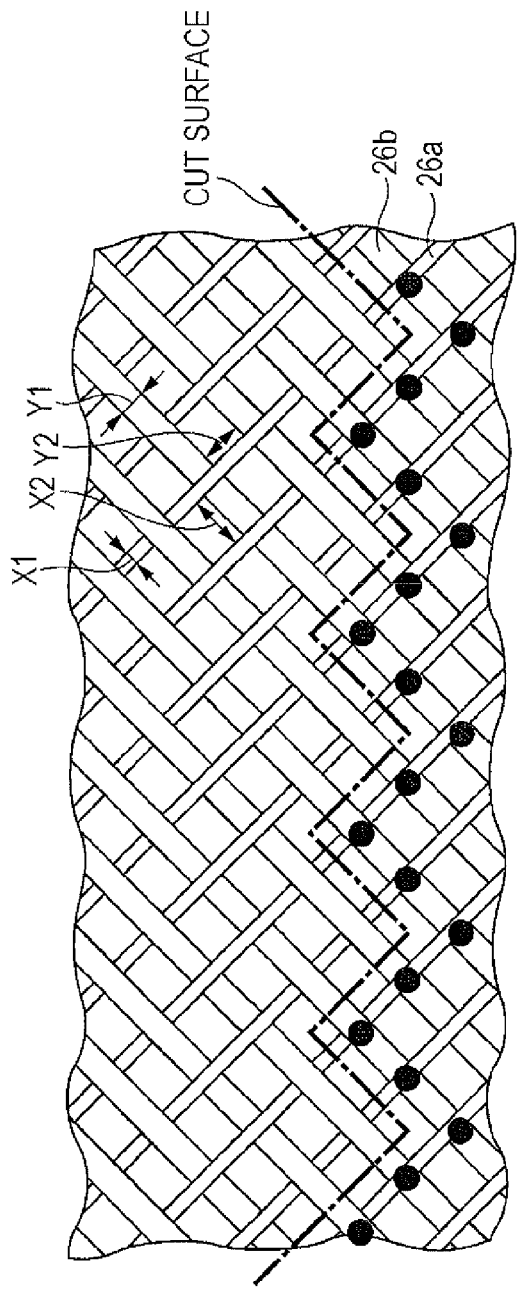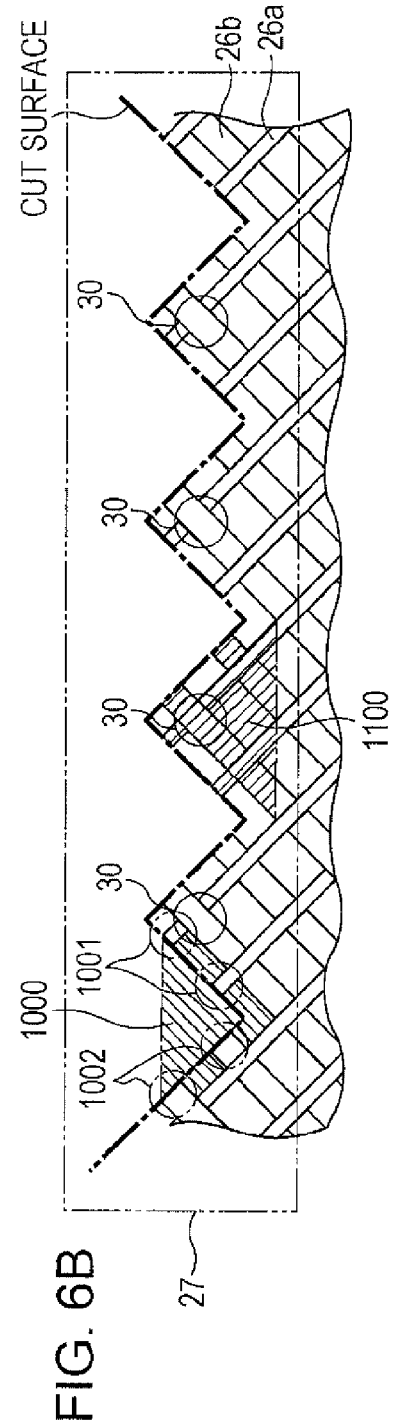
FIG. 6A
FIG. 6B

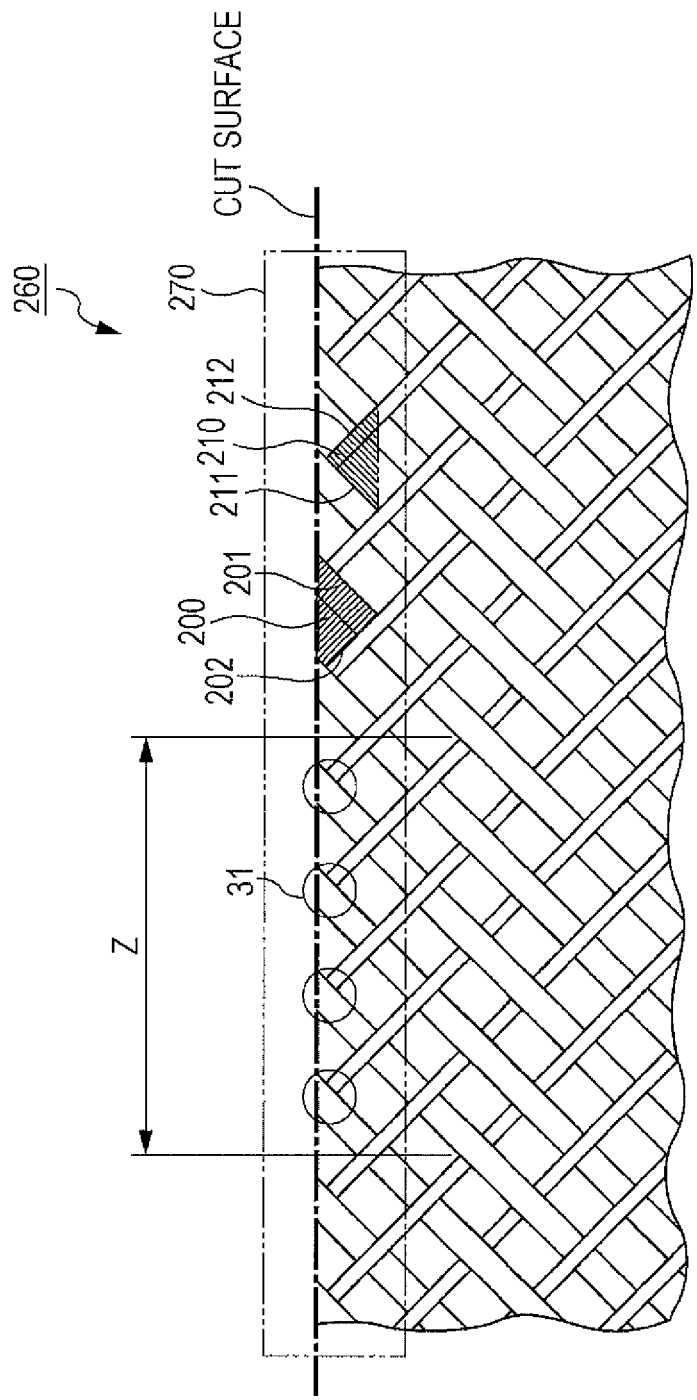

CATHETER

CROSS-REFERENCE TO RELATED APPLICATION

The present application claims priority to Japanese Patent Application No. 2012-167990 filed in the Japan Patent Office on Jul. 30, 2012, the entirety of which is hereby incorporated by reference.

BACKGROUND OF THE INVENTION

1. Field of the Invention

The disclosed embodiments relate to medical devices. More specifically, the disclosed embodiments relate to catheters that are inserted into blood vessels or the like.

2. Description of Related Art

A catheter that is inserted into a tubular organ, such as a blood vessel, an alimentary canal, or a ureter, or an internal bodily tissue, structurally includes an inner layer (base tube) made of a resin, an outer layer surrounding the outer periphery of the inner layer and made of a resin, and a braid (reinforcement layer) interposed between the inner layer and the outer layer. This braid is formed by weaving wires made of a metal such as copper or stainless steel together in consideration of properties required for a catheter, such as pushability, torque transfer capability, and pressure resistance (see Japanese Unexamined Patent Application Publication No. 2001-87389, for example).

If such a braid were to extend up to a distal end portion of a catheter, the distal end portion of the catheter would have no flexibility. In view of this, a catheter having a distal end portion that is made flexible by cutting part of the braid (see Japanese Unexamined Patent Application Publication No. 2011-72562, for example) has been developed. In addition, a catheter has been developed in which an area over which a distal tip made of a resin is bonded to a distal end portion of the catheter is increased by partially cutting off the distal end portion of the catheter such that the distal end portion of the catheter has a slope so that the distal tip and the distal end portion of the catheter may be highly reliably bonded together (see U.S. Pat. No. 5,509,910, for example).

In the above structure, however, since part of the braid in the distal end portion of the catheter is completely cut off, the intrinsic pushability or torque transfer capability of the catheter is reduced. In addition, even if the distal end portion of the catheter is obliquely cut, the distal tip is mainly bonded to only the outer layer due to the presence of the braid, thereby negligibly improving the tensile strength of the distal tip.

As illustrated in FIG. 7, since the distal end portion of an existing braid is cut by a laser beam or the like, the distal end portion has fine projections and depressions arranged in the circumferential direction of the catheter. When the catheter is pushed through an object, the distal end portion of the braid penetrates the distal tip in some cases because there are a large number of projections formed in the distal end portion of the braid. Particularly, in the case where a catheter required to be small for reducing a patient treatment burden has a distal tip having a small thickness or a short length, such a problem is more likely to occur.

SUMMARY

The present invention has been developed in view of the above circumstances and provides a catheter having an excellent pushability and an excellent torque transfer capability, the catheter including a distal tip having a high tensile strength, and a braid having a distal end portion that does not penetrate the distal tip even when the distal tip has a small thickness and a short length.

The following measures are taken to produce the above catheter.

According to an aspect of the present invention, a catheter includes an inner layer made of a resin; a braid surrounding an outer periphery of the inner layer, the braid including a plurality of first wires and a plurality of second wires; an outer layer surrounding an outer periphery of the braid, the outer layer being made of a resin; and a distal tip disposed at a distal end of the inner layer, a distal end of the braid, and a distal end of the outer layer, the distal tip being made of a resin. A recessed region is formed in a distal end portion of the braid, the recessed region having a recess first side and a recess second side, a length the recess first side being longer than a sum of a wire width of one of the first wires and a distance between two adjacent first wires among the plurality of first wires, a length of the recess second side being longer than a sum of a wire width of one of the second wires and a distance between two adjacent second wires among the plurality of second wires. The distal tip is bonded to the inner layer in the recessed region.

In the catheter according to the aspect of the present invention, a recessed region defined by a recess first side and a recess second side is formed in a distal end portion of the braid, a length of the recess first side being longer than the sum of a wire width of one first wire and a distance between two adjacent first wires, a length of the recess second side being longer than the sum of a wire width of one second wire and a distance between two adjacent second wires. Since the distal tip made of a resin adheres to the inner layer made of a resin in the recessed region, the area over which the distal tip is bonded to the inner layer is significantly increased, and thus the tensile strength of the distal tip is improved. In addition, since a length of each of the recess first sides and the recess second sides is longer than the sum of the wire width of one of the first or second wires and a distance between two adjacent first or second wires, the number of peaks formed in the distal end portion of the braid can be made smaller than that in the existing case. Consequently, it becomes less likely that the distal end portion of the braid will penetrate the distal tip when the catheter is pushed through a body. Thus, the thickness or the length of the distal tip can be reduced, thereby achieving size reduction of the distal tip.

BRIEF DESCRIPTION OF THE DRAWINGS

FIG. 1 illustrates the entirety of a catheter according to an embodiment.

FIG. 2 illustrates a distal end portion of the catheter in an enlarged manner, from which a distal tip is excluded for ease of illustration.

FIG. 4 is a cross-sectional view of the distal end portion of the catheter and the distal tip.

FIGS. 6A and 6B are plan views of a distal end portion of a braid according to another embodiment that is cut along a surface different from the surface along which the distal end portion of the braid illustrated in FIGS. 3A and 3B is cut.

FIG. 7 is a plan view of a distal end portion of an existing braid.

DETAILED DESCRIPTION OF EMBODIMENTS

Figure 3A:
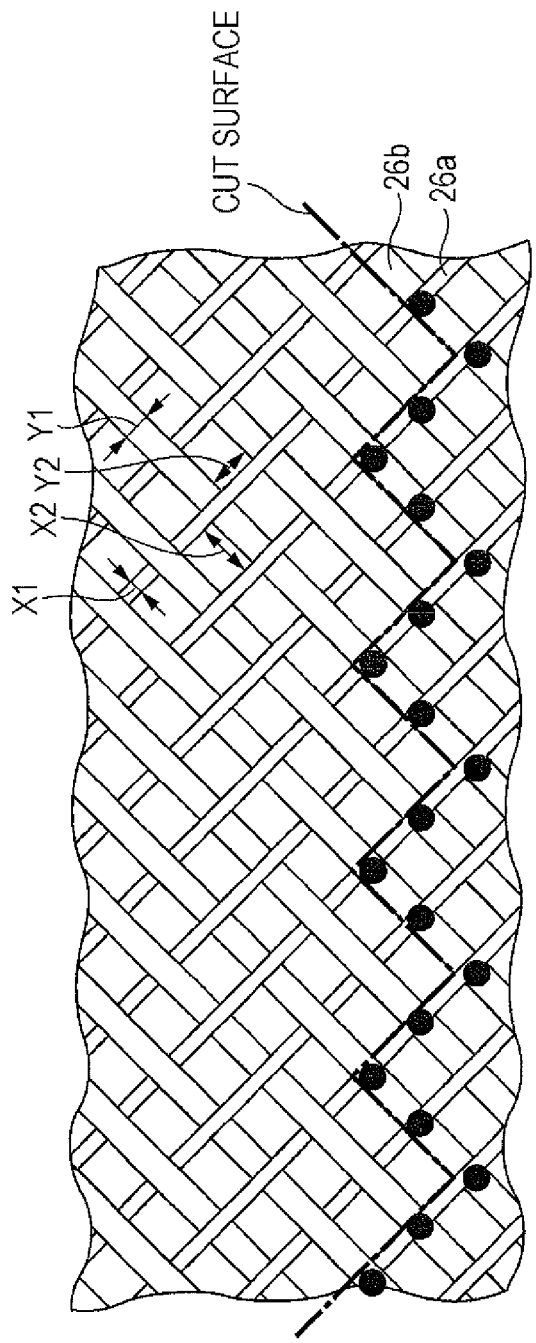
FIG. 3A is a plan view of a distal end portion of a braid before being cut and FIG. 3B is a plan view of the distal end portion of the braid after being cut.

Referring to FIGS. 1 to 7, a catheter 1 according to an embodiment will be described as an example. In FIGS. 1, 2, and 4, the left side is a distal side (far side) that is inserted into a body while the right side is a proximal side (a near side or a base side) that is manipulated by a technician such as a doctor. For ease of understanding, small components such as first wires 26a and second wires 26b of a braid 26, which are described below, are slightly exaggerated throughout the drawings relative to the dimensions of other components.

The catheter 1 illustrated in FIG. 1 is a tubular medical device having a full length of approximately 1200 mm. The catheter 1 mainly includes a catheter body 10 having flexibility, a distal tip 12 bonded to a distal end portion 11 of the catheter body 10, and a connector 14 fixed to a proximal portion of the catheter body 10.

As illustrated in the enlarged view of FIG. 2 and the cross sectional view of FIG. 4, the catheter body 10 includes an inner layer 24, a braid 26 serving as a reinforcement member, and an outer layer 28, which are radially arranged in this order from the inside.

The inner layer 24 is made of a resin and defines a lumen 18 through which a guide wire or another catheter is inserted. The resin material that the inner layer 24 is made of is not particularly limited, but polytetrafluoroethylene (PTFE) is employed in the embodiment.

A braid 26, which serves as a reinforcement member, surrounds the outer periphery of the inner layer 24. As illustrated in FIGS. 2, 3A, 3B, 6A, and 6B, the braid 26 is obtained by weaving first wires 26a and second wires 26b into a net (i.e., into a mesh). In this embodiment, eight first wires 26a and eight second wires 26b, that is, 16 (8+8) wires are alternately woven together. In other words, the first wires 26a are wound in one direction while the second wires 26b are wound in another direction.

Figure 3B:
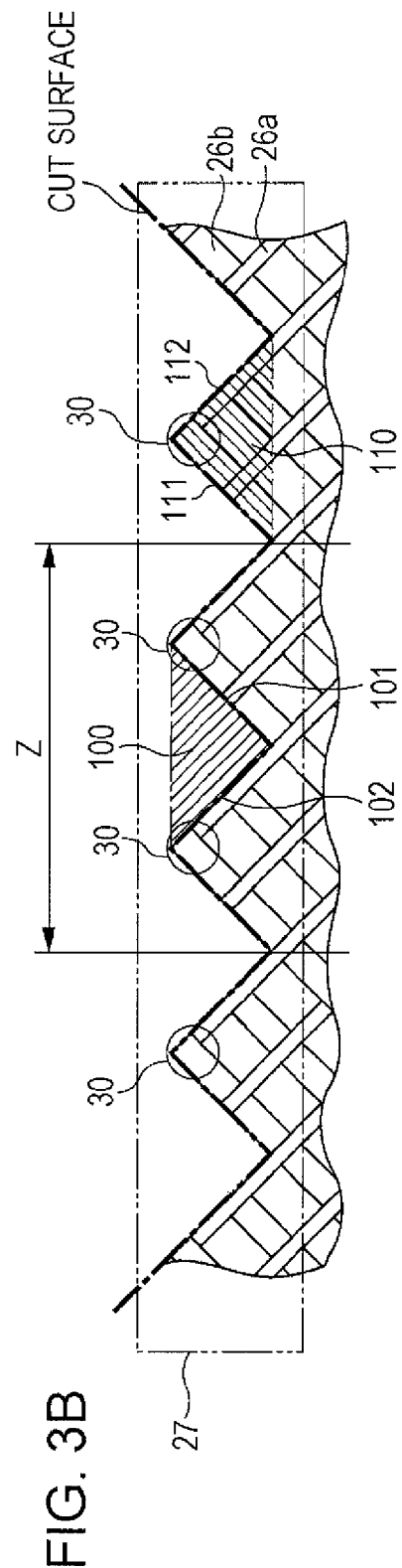

The combination of wires of the braid is not limited to the above example of 8+8 wires. The combination may be a balanced combination, such as 4+4 wires or 2+2 wires, or an unbalanced combination, such as 4+8 wires or 2+4 wires. The wire width of the first wires 26a and the wire width of the second wires 26b may be the same or different. In FIGS. 3A and 3B, the first wires 26a and the second wires 26b are woven such that the first wires 26a alternately cross over two second wires 26b (every other second wire 26b) and then cross under two second wires 26b. Alternatively, the first wires 26a and the second wires 26b may be woven such that the first wires 26a alternately cross over one second wire 26b and then cross under one second wire 26b.

The first wires 26a and the second wires 26b may be made of the same material or different materials. In this embodiment, the first wires 26a made of tungsten and the second wires 26b made of stainless steel (Japanese Industrial Standards (JIS) No. SUS316) are used. However, wires may be made of materials other than metals, such as reinforced plastics. In this embodiment, the cross sectional shape of the first wires 26a and the second wires 26b may be circular or rectangular.

The outer layer 28, which is made of a resin, surrounds the outer periphery of the braid 26 and covers the inner layer 24 and the braid 26. The resin material that the outer layer 28 is made of is not particularly limited and may be polyamide, a polyamide-based elastomer, polyester, polyurethane, or the like.

As illustrated in the cross sectional view of FIG. 4, a portion of the catheter body 10 is covered by the outer layer 28, the portion excluding a portion of the catheter body 10 having a length equivalent to the length L of the distal tip 12 from a tip opening 15 of the catheter body 10. The outer layer 28 is made of resin materials having different hardnesses such that the catheter 10 becomes increasingly more flexible from the proximal side toward distal side. As illustrated in the cross sectional view of FIG. 4, the braid 26 is covered by a resin-made middle layer 29 and the resin-made outer layer 28, but is not limited to this structure. The catheter body 10 may be formed without using the middle layer 29 so that the outer diameter of the catheter 1 can be reduced. The middle layer 29 may be made of a resin material that is the same as or different from the resin material of the inner layer 24 or the outer layer 28.

In the cross sectional view of FIG. 4, the distal end portion 11 of the catheter body 10 has a uniform inner diameter in the axial direction, but is not limited to this structure. Only the distal end portion 11 of the catheter body 10 may have a tapered shape such that the inner diameter is widened toward the proximal end of the catheter body 10.

The distal tip 12, which is made of a resin, is attached to a distal end of the catheter body 10. The distal tip 12 is a cylindrical member having the tip opening 15. The resin that the distal tip 12 is made of is not particularly limited and may be polyurethane, a polyurethane-based elastomer, or the like. The distal tip 12 may contain a radiopaque powder. For example, if the distal tip 12 contains approximately 65 wt % to approximately 90 wt % of a radiopaque powder (tungsten powder, for example), a technician such as a doctor can accurately recognize the position of the catheter during coronary artery imaging.

Subsequently, the distal end portion 27 of the braid 26 is described.

As illustrated in FIGS. 3A and 3B, the wire width of the first wires 26a is denoted by X1 and the distance between two adjacent first wires 26a is denoted by X2. The wire width of the second wires 26b is denoted by Y1 and the distance between two adjacent second wires 26b is denoted by Y2. When the first wires 26a and the second wires 26b are woven together, the distance between two adjacent wires may vary depending on positions but it is preferable that the first wires 26a be woven at equal intervals of X2 and the second wires 26b be woven at equal intervals of Y2. Alternatively, the wire width Y1 of the second wires 26b may be the same as the wire width X1 of the first wires 26a or the distance Y2 between two adjacent second wires 26b may be the same as the distance X2 between two adjacent first wires 26a. In other words, the wire width of the first wires 26a or the second wires 26b and the distance between two adjacent first wires 26a or second wires 26b may be appropriately determined.

Recessed regions 100 each defined by a first side 101, which is longer than the sum of the wire width X1 of each first wire 26a and the distance X2 between two adjacent first wires 26a, and a second side 102, which is longer than the sum of the wire width Y1 of each second wire 26b and the distance Y2 between two adjacent second wires 26b, are formed in the distal end portion 27 of the braid 26. In this embodiment, the length of the first side 101 is (X1+X2)×2 and the length of the second side 102 is (Y1+Y2)×2.

Protruding regions 110 are formed on both sides of each recessed region 100. Each protruding region 110 is defined by a first side 111, which is longer than the sum of the wire width X1 of each first wire 26a and the distance X2 between two adjacent first wires 26a, and a second side 112, which is longer than the sum of the wire width Y1 of each second wire 26b and the distance Y2 between two adjacent second wires 26b. In this embodiment, as in the case of each recessed region 100, the length of the first side 111 is (X1+X2)×2 and the length of the second side 112 is (Y1+Y2)×2.

As illustrated in FIG. 7, the existing braid 260 has a distal end portion 270 having fine recesses and protrusions, that is, fine recessed regions 200 and fine protruding regions 210. The length of a first side 201 of each recessed region 200 is equal to the sum of the width X1 and the distance X2 and the length of a second side 202 of the recessed region 200 is equal to the sum of the width Y1 and the distance Y2. Likewise, the length of a first side 211 of each protruding region 210 is equal to the sum of the width X1 and the distance X2 and the length of a second side 212 of the protruding region 210 is equal to the sum of the width Y1 and the distance Y2.

The area of each recessed region 200 of the existing braid 260 is calculated by (X1+X2)×(Y1+Y2)/2. The area of each recessed region 100 according to the embodiment is calculated by {(X1+X2)×2}×{(Y1+Y2)×2}/2. Thus, the area over which the distal tip 12 is bonded to the inner layer 24 is four times that in the existing case. In this manner, by forming the recessed regions 100 each having the first side 101 and the second side 102, each of which is longer than the sum of the wire width of each first or second wire and the distance between two adjacent first or second wires, the area over which the distal tip 12 is bonded to the inner layer 24 can be increased. Consequently, it becomes less likely that the distal tip 12 will be detached.

Since part of each first wire 26a and part of each second wire 26b are removed so as not to protrude into the recessed regions 100 of braid 26, the distal end portion 27 of the braid 26 can have flexibility.

As illustrated in FIG. 3B, two peaks 30 are included in a range of the distal end portion 27 of the braid 26 having a length Z in the circumferential direction. Each peak 30 is defined by one first wire 26a and one second wire 26b. On the other hand, as illustrated in FIG. 7, four peaks 31, each defined by one first wire 26a and one second wire 26b, are included in a range of the distal end portion 270 of the existing braid 260 having the length Z in the circumferential direction. Thus, the number of peaks 30 in the distal end portion 27 can be reduced by forming the protruding regions 110 each having one first side 111 and one second side 112, each of which is longer than the sum of the wire width of each first or second wire and the distance between two adjacent first or second wires. Thus, it becomes less likely that the distal end portion 27 of the braid 26 will penetrate the distal tip 12 when a technician such as a doctor pushes the catheter 1 through a meandering blood vessel while the distal end portion 11 of the catheter body 10 is bent in accordance with the meandering blood vessel.

As a result of the increase in the area over which the distal tip 12 is bonded to the inner layer 24 and the reduction of the number of peaks 30 in the distal end portion 27 of the braid 26, the length of the distal tip 12 in the axial direction can be reduced and the thickness of the distal tip 12 can be reduced.

Figure 5A:
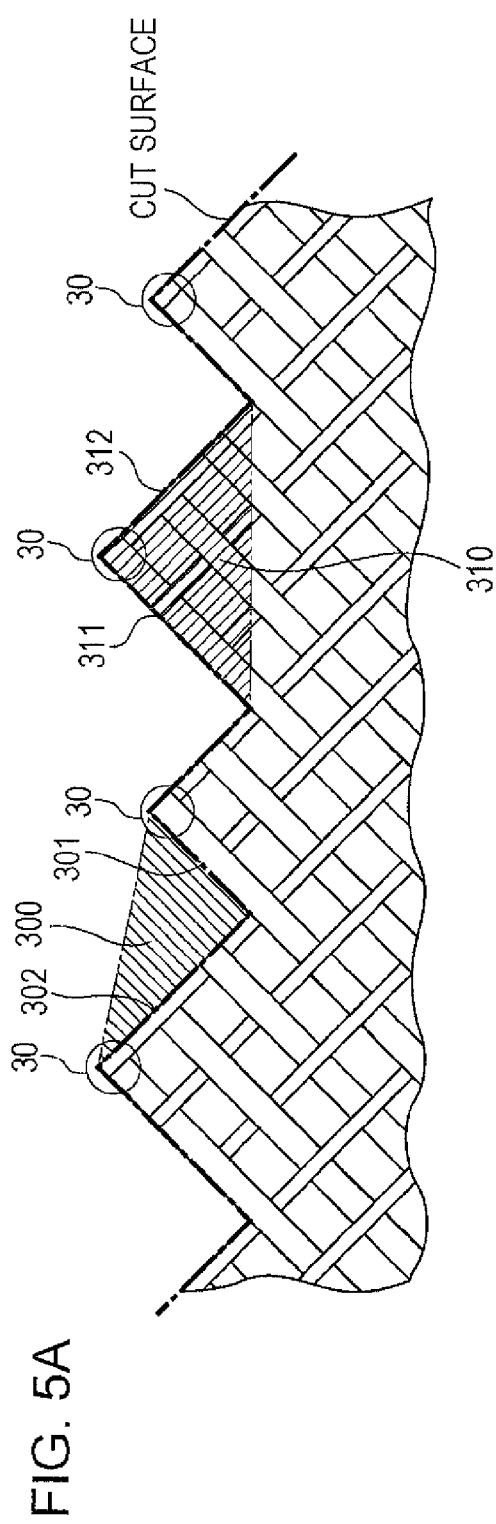
FIGS. 5A and 5B are plan views of distal end portions of braids according to other embodiments after being cut.

The sizes or the shapes of the recessed regions 100 and the protruding regions 110 formed in the distal end portion 27 of the braid 26 are not limited to those illustrated in FIG. 3B. For example, as illustrated in FIG. 5A, recessed regions 300 and protruding regions 310 may have different sizes. Moreover, as illustrated in FIG. 5B, quadrangular recessed regions 400 and quadrangular protruding regions 410 may be employed.

Figure 5B:
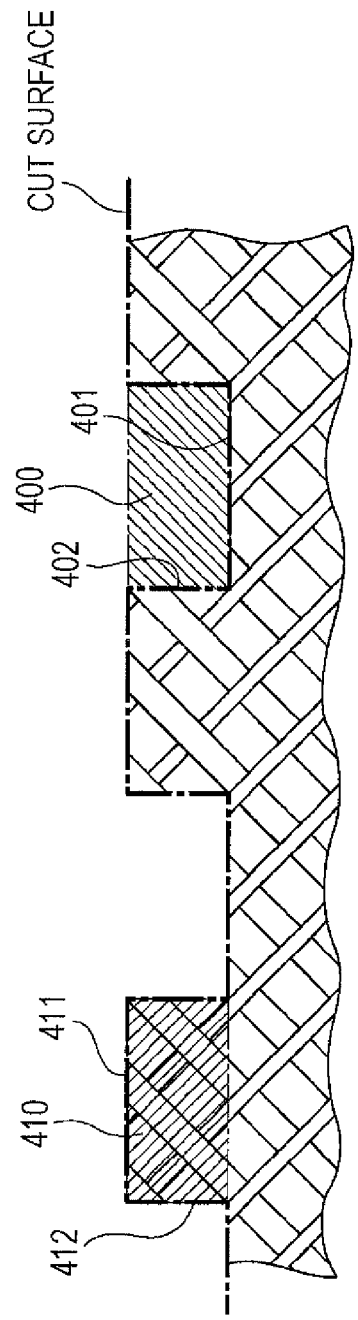

As in the case of the recessed regions 100, as illustrated in FIGS. 5A and 5B, a first side 301 of each recessed region 300 and a first side 401 of each recessed region 400 have a length that is longer than the sum of the wire width X1 of each first wire 26a and the distance X2 between two adjacent first wires 26a. A second side 302 of each recessed region 300 and a second side 402 of each recessed region 400 have a length that is longer than the sum of the wire width Y1 of each second wire 26b and the distance Y2 between two adjacent second wires 26b. In addition, as in the case of the protruding regions 110, a first side 311 of each protruding region 310 and a first side 411 of each protruding region 410 have a length that is longer than the sum of the wire width x1 of each first wire 26a and the distance X2 between two adjacent first wires 26a. A second side 312 of each protruding region 310 and a second side 412 of each protruding region 410 have a length that is longer than the sum of the wire width Y1 of each second wire 26b and the distance Y2 between two adjacent second wires 26b.

In FIG. 3B, the first sides 101 of the recessed regions 100 and the first sides 111 of the protruding regions 110 are defined by the second wires 26b. The second sides 102 of the recessed regions 100 and the second sides 112 of the protruding regions 110 are defined by the first wires 26a. Since the first wires 26a and the second wires 26b do not jut into the recessed regions 100, the area over which the distal tip 12 is bonded to the inner layer 24 can be increased.

The shape of the distal end portion 27 of the braid 26, however, is not limited to the one illustrated in FIG. 3B. As illustrated in FIG. 6B, recessed regions 1000 each having recesses so as to correspond to protruding end portions of the first wires 26a and the second wires 26b may be employed. As illustrated in FIG. 6B, since each recessed region 1000 has the recesses corresponding to protruding end portions 1001 of the first wires 26a and protruding end portions 1002 of the second wires 26b, the area over which the distal tip 12 is bonded to the inner layer 24 is smaller than the area illustrated in FIG. 3B. Nevertheless, as in the case illustrated in FIG. 3B, the number of peaks 30 formed in the distal end portion 27 of the braid 26 can be reduced. Thus, the distal tip 12 can be made smaller. As described below, since the recessed regions 100 and the protruding regions 110 are formed by irradiating unnecessary portions of the first wires 26a and the second wires 26b in the distal end portion 27 of the braid 26 with a laser beam, conditions of the laser beam (the intensity or the position of the beam) with which the first wires 26a and the second wires 26b are irradiated need to be optimized so that the shape illustrated in FIG. 3B is formed. In contrast, when the shape illustrated in FIG. 6B is formed, the irradiation conditions of a laser beam used to form the recessed regions 1000 and the protruding regions 1100 do not need to be optimized, and thus the distal end portion 27 of the braid 26 can be easily formed.

As illustrated in FIGS. 2 and 3B, in this embodiment, multiple recessed regions 100 and multiple protruding regions 110 are arranged in the circumferential direction of the braid 26 and the size of the recessed regions 100 and the size of the protruding regions 110 are the same. Therefore, the distal end portion 27 of the braid 26 can have a strength that is uniform in the circumferential direction, thereby providing a stable cylindrical braid 26.

In addition, since the distal tip 12 is uniformly bonded to the inner layer 24 in the circumferential direction in the recessed regions 100, it becomes less likely that the distal tip 12 will be detached from the distal end portion 11 of the catheter body 10 when the distal end portion 11 of the catheter body 10 is bent inside a meandering blood vessel. In this embodiment in particular, since the distal tip 12 has a high tensile strength, it becomes less likely that the distal tip 12 will be detached from the distal end portion 11 of the catheter body 10 when a technician such as a doctor removes the catheter 1 from the body after treatment.

Now, a method of manufacturing the distal end portion 27 of the braid 26 is described. Although a description is given based on FIGS. 3A and 3B here, methods of manufacturing the distal end portions 27 of the braids 26 illustrated in FIGS. 5A, 5B, and 6B according to other embodiments are basically the same. Thus, the methods of manufacturing the distal end portions illustrated in FIGS. 5A, 5B, and 6B are not described here.

First, the inner layer 24 and the braid 26 are formed on a core. In this state, intersection points of the first wires 26a and the second wires 26b of the braid 26 and the vicinity of the intersection points are irradiated with a laser beam, so that the first wires 26a and the second wires 26b are joined together at or around the intersection points (indicated by filled circles in FIG. 3A). Then, a laser beam is emitted again along the joined first wires 26a and the second wires 26b, so that unnecessary portions of the first wires 26a and the second wires 26b are cut off. In this manner, the recessed regions 100 and the protruding regions 110 can be formed in the distal end portion 27 of the braid 26.

Although the first wires 26a and the second wires 26b are cut after being joined together in the embodiment, the present invention is not limited to this procedure. The first wires 26a and the second wires 26b may be joined and cut at the same time by regulating irradiation conditions of a laser beam. In contrast, the portions of the first wires 26a and the second wires 26b that are to be cut off may be determined in advance and the first wires 26a and the second wires 26b may be cut accordingly before the intersection points of the first wires 26a and the second wires 26b and the vicinities of the intersection points are irradiated with a laser beam so that the first wires 26a and the second wires 26b are joined together.

The laser beam used here is not particularly limited. In this embodiment, an yttrium aluminum garnet (YAG) pulsed laser is used.

Subsequently, a resin-made tube, which is to serve as the outer layer 28, is covered around the outer periphery of the braid 26 and heated to a predetermined temperature so as to melt and adhere to the braid 26. The outer layer 28 is caused to adhere to a portion of the braid 26 excluding the distal end portion 27 of the braid 26. Thus, the outer layer 28 is not formed in the recessed regions 100 and the protruding regions 110.

Then, a resin-made tube, which is to serve as the distal tip 12, is covered around the distal end portion 27 of the braid 26 and heated to a predetermined temperature so as to melt and adhere to the distal end portion 27. Thus, the distal tip 12 is caused to adhere to the side surface of the outer layer 28 and the upper surface of the inner layer 24 in the recessed regions 100, which are formed in the distal end portion 27 of the braid 26.

Thereafter, when the core is removed, a catheter including the distal end portion 11 of the catheter body 10 and the distal tip 12 can be obtained.

Although the outer layer 28 is caused to adhere to the braid 26 after the recessed regions 100 and the protruding regions 110 are formed in this embodiment, the present invention is not limited to this procedure. The inner layer 24, the braid 26, and the outer layer 28 may be formed first, a portion of the outer layer 28 located in the distal end portion 27 of the braid 26 may then be removed by a process such as brushing, an exposed portion of the distal end portion 27 of the braid 26 may be irradiated with a laser beam to form the recessed regions 100 and the protruding regions 110, and finally the distal tip 12 may be caused to melt and adhere to the outer layer 28 and the inner layer 24.

The first wires 26a and the second wires 26b are joined together in the protruding region 10. Thus, the distal end portion 27 of the braid 26 can be prevented from being expanded by being cut and from becoming loose, thereby increasing the area over which the distal tip 12 is bonded to the inner layer 24. In addition, by joining the first wires 26a and the second wires 26b together in the protruding region 10, the braid 26 is prevented from becoming loose up to the distal end, thereby improving the pushability and the capability to transmit torque of the catheter.

As described above, in this embodiment, the recessed regions 100 each defined by the first side 101 and the second side 102 are formed in the distal end portion 27 of the braid 26, the first side 101 being longer than the sum of the wire width X1 of each first wire 26a and the distance X2 between two adjacent first wires 26a, the second side 102 being longer than the sum of the wire width Y1 of each second wire 26b and the distance Y2 between two adjacent second wires 26b. In addition, the protruding regions 110 each defined by the first side 111 and the second side 112 are formed in the distal end portion 27 of the braid 26, the first side 111 being longer than the sum of the wire width X1 of each first wire 26a and the distance X2 between two adjacent first wires 26a, the second side 112 being longer than the sum of the wire width Y1 of each second wire 26b and the distance Y2 between two adjacent second wires 26b. Thus, the area over which the distal tip 12 is bonded to the inner layer 24 is increased and the number of peaks 30 is reduced. Thus, the length of the distal tip 12 in the axial direction can be reduced and the thickness of the distal tip 12 can be reduced, thereby achieving size reduction of the distal tip 12.

What is claimed is:

1. A catheter comprising:
    an inner layer made of a resin;
    a braid surrounding an outer periphery of the inner layer, the braid including a plurality of first wires and a plurality of second wires;
    an outer layer surrounding an outer periphery of the braid, the outer layer being made of a resin; and
    a distal tip disposed at a distal end of the inner layer, a distal end of the braid, and a distal end of the outer layer, the distal tip being made of a resin,
    wherein
    a recessed region is formed in a distal end portion of the braid, the recessed region having a recess first side and a recess second side,
    a length of the recess first side is longer than a sum of a wire width of one of the plurality of first wires and a distance between two adjacent first wires among the plurality of first wires,
    a length of the recess second side is longer than a sum of a wire width of one of the plurality of second wires and a distance between two adjacent second wires among the plurality of second wires, and
    the distal tip is bonded to the inner layer in the recessed region.

2. The catheter according to claim 1, wherein
    a protruding region is formed in the distal end portion of the braid, the protruding region having a protrusion first side and a protrusion second side,
    a length of the protrusion first side is longer than a sum of a wire width of one of the plurality of first wires and a distance between two adjacent first wires among the plurality of first wires,
    a length of the protrusion second side is longer than a sum of a wire width of one of the plurality of second wires and a distance between two adjacent second wires among the plurality of second wires, the recess first side and the protrusion first side are defined by one of the plurality of first wires, and the recess second side and the protrusion second side are defined by one of the plurality of second wires.

3. The catheter according to claim 2, further comprising:
a plurality of the recessed regions and a plurality of the protruding regions such that the plurality of recessed regions and the plurality of protruding regions are arranged in a circumferential direction of the braid,
wherein a size of each of the plurality of recessed regions is the same as a size of each of the plurality of protruding regions.

4. The catheter according to claim 3, wherein the first wires and the second wires are joined together in the protruding regions at intersection points at which the first wires and the second wires cross one another.

5. The catheter according to claim 2, wherein the first wires and the second wires are joined together in the protruding region at intersection points at which the first wires and the second wires cross one another.

6. A catheter having a proximal end and a distal end, comprising:
an inner layer;
a braid surrounding an outer periphery of the inner layer, the braid including a plurality of first wires and a plurality of second wires;
an outer layer surrounding an outer periphery of the braid; and
a tip disposed at the distal end of the catheter,
wherein
the plurality of first wires and the plurality of second wires are woven together in a mesh structure,
a distal end portion of the braid includes a plurality of protruding regions and a plurality of recessed regions, each of the plurality of protruding regions having a protrusion first side and a protrusion second side,
a length of the protrusion first side is longer than a sum of a wire width of one of the plurality of first wires and a distance between two first wires of the plurality of first wires, and
a length of the protrusion second side is longer than a sum of a wire width of one of the plurality of second wires and a distance between two second wires of the plurality of second wires.

7. The catheter according to claim 6, wherein each of the plurality of recessed regions has a recess first side and a recess second side.

8. The catheter according to claim 7, wherein
a length of the recess first side is longer than the sum of the wire width of one of the plurality of first wires and the distance between two first wires of the plurality of first wires, and
a length of the recess second side is longer than the sum of the wire width of one of the plurality of second wires and the distance between two second wires of the plurality of second wires.

9. The catheter according to claim 7, wherein
the length of the recess first side is equal to the length of the protrusion first side, and
the length of the recess second side is equal to the length of the protrusion second side.

10. The catheter according to claim 7, wherein
the recess first side and the protrusion first side are each defined by one of the plurality of first wires, and
the recess second side and the protrusion second side are each defined by one of the plurality of second wires.

11. The catheter according to claim 6, wherein
the plurality of recessed regions and the plurality of protruding regions are arranged in a circumferential direction around the distal end portion of the braid, and
a size of each of the plurality of recessed regions is the same as a size of each of the plurality of protruding regions.

12. The catheter according to claim 6, wherein one of the plurality of first wires crosses one of the plurality of second wires at a tip portion of each of the plurality of protruding regions.

13. The catheter according to claim 6, wherein one of the plurality of first wires does not cross one of the plurality of second wires at a tip portion of each of the plurality of protruding regions.

14. The catheter according to claim 6, wherein the tip of the catheter is bonded to:
a side surface of the outer layer,
at least one of the plurality of protruding regions of the braid, and
an upper surface of the inner layer in the plurality of recessed regions of the braid.

* * * * *